United States Patent
Bang et al.

(10) Patent No.: US 10,416,349 B2
(45) Date of Patent: Sep. 17, 2019

(54) PHASE PREDICTIONS USING GEOCHEMICAL DATA

(71) Applicant: CONOCOPHILLIPS COMPANY, Houston, TX (US)

(72) Inventors: Vishal Bang, Houston, TX (US); Olufemi A. Jokanola, Richmond, TX (US)

(73) Assignee: CONOCOPHILLIPS COMPANY, Houston, TX (US)

( * ) Notice: Subject to any disclaimer, the term of this patent is extended or adjusted under 35 U.S.C. 154(b) by 211 days.

(21) Appl. No.: 15/263,501

(22) Filed: Sep. 13, 2016

(65) Prior Publication Data

US 2017/0075028 A1 Mar. 16, 2017

Related U.S. Application Data (60) Provisional application No. 62/218,738, filed on Sep. 15, 2015.

(51) Int. Cl.
- *G01V 99/00* (2009.01)
- *G01V 9/00* (2006.01)
- *G01N 33/28* (2006.01)

(52) U.S. Cl.
CPC ......... *G01V 99/00* (2013.01); *G01N 33/2823* (2013.01); *G01V 9/007* (2013.01)

(58) Field of Classification Search
CPC .................................................... G01V 11/002
See application file for complete search history.

(56) References Cited

U.S. PATENT DOCUMENTS

| | | | |
|---|---|---|---|
| 8,666,667 B2 | 3/2014 | Michael et al. | |
| 2009/0071239 A1 | 3/2009 | Rojas et al. | |
| 2009/0235731 A1* | 9/2009 | Zuo .......... | E21B 49/08 73/152.28 |
| 2011/0246143 A1* | 10/2011 | Pomerantz .......... | E21B 49/00 703/2 |
| 2012/0150519 A1 | 6/2012 | Bang et al. | |
| 2012/0296617 A1* | 11/2012 | Zuo .......... | E21B 47/10 703/10 |
| 2013/0151159 A1* | 6/2013 | Pomerantz .......... | E21B 49/082 702/11 |
| 2013/0197808 A1* | 8/2013 | Zuo .......... | E21B 47/00 702/6 |
| 2015/0006084 A1* | 1/2015 | Zuo .......... | E21B 49/00 702/13 |

FOREIGN PATENT DOCUMENTS

WO 2014025342 8/2012

OTHER PUBLICATIONS

International Search Report for parent case, App. No. PCT/US2016/051529, dated Dec. 20, 2016.

* cited by examiner

*Primary Examiner* — Manuel L Barbee
*Assistant Examiner* — Raymond L Nimox
(74) *Attorney, Agent, or Firm* — ConocoPhillips Company (57) ABSTRACT

Methods for developing equation-of-states (EOS) composition models for predicting petroleum reservoir fluid behavior and understanding fluid heterogeneity in unconventional shale plays are described. In particular, limited geochemical data from samples taken from the reservoir of interested are utilized to build and tune the EOS model and improve predictions. Real-time applications are also described.

22 Claims, 7 Drawing Sheets

Indication of a Dew Point- n_dew = 21
Indication of a Bubble Point n_bubble = 42
Total sample run n_sample - 63
67% chance of given a Bubble Point
hence classified as an OIL WELL Psat
P mean-4126 psi
P50- 4102 psi
P mode- 4120 psi
Measured – 4170 psi

FIGURE 8

Psat
P mean-4524 psi
P50- 4500 psi
P mode- 4320 psi
Measured – ?? psi

PHASE PREDICTIONS USING GEOCHEMICAL DATA

PRIOR RELATED APPLICATIONS

This application is a non-provisional application which claims benefit under 35 USC § 119(e) to U.S. Provisional Application Ser. No. 62/218,738 filed Sep. 15, 2015, entitled "PHASE PREDICTIONS USING GEOCHEMICAL DATA," which is incorporated herein in its entirety.

FIELD OF THE DISCLOSURE

The disclosure relates to methods for predicting petroleum reservoir fluid phase behavior and properties, in particular methods for the compositional approach to modeling.

BACKGROUND OF THE DISCLOSURE

Understanding the phase behavior of the various fluids present in a petroleum reservoir is essential for achieving optimal design and cost-effective operations in a petroleum development. Computer-based modeling techniques have been developed for estimating the properties and/or phase behavior of petroleum fluid in a reservoir of interest. The calculation of phase behavior in a reservoir model can be made in one of the two following ways: 1) using a "black-oil" approach based on simple interpolation of pressure, volume and temperature (PVT) properties as a function of pressure, or 2) using a "compositional" approach based on a thermodynamically-consistent model such as a cubic equation of state (EOS).

The main difference between these two methods is that a black oil simulator does not consider changes in composition of the hydrocarbons as the field is produced, whereas the compositional model fits the PVT properties of oil and gas phases to an equation of state (EOS) as a mixture of components. The compositional simulator then uses the tuned EOS model to dynamically track the movement of both phases and components in field. Thus, depletion of e.g. gas-condensate reservoirs and volatile-oil reservoirs can be accounted for in the compositional model.

Phase behavior of a fluid with known composition consists of defining the number of phases, phase amounts, phase compositions, phase properties (molecular weight, density, and viscosity), and the interfacial tension (IFT) between phases. In addition to defining the phase behavior of a fluid at a specific reservoir pressure, knowing the derivatives of all phase properties with respect to pressure, temperature and composition is important in reservoir simulation. Thus, compositional modeling is much more complex and difficult than the more simplified black oil techniques.

Typically, compositional modeling of phase behaviors employs an equation of state (EOS) model that represents the phase behavior of the petroleum fluid in the reservoir. Once the EOS model is defined, it can be used to compute a wide array of properties of the petroleum fluid of the reservoir, such as gas-oil ratio (GOR) or condensate-gas ratio (CGR) (one is the inverse of the other), density of each phase, volumetric factors and compressibility, and saturation pressure (bubble or dew point). Transport properties, such as viscosity, can also be obtained using the EOS model and standard viscosity correlations, such as Lohrenz-Bray-Clark (LBC) correlations. Furthermore, the EOS model can be extended with other reservoir evaluation techniques for compositional simulation of flow and production behavior of the petroleum fluid of the reservoir, as is well known in the art.

For example, compositional simulations can be helpful in studying (1) depletion of a volatile oil or gas condensate reservoir where phase compositions and properties vary significantly with pressure below bubble or dew point pressures, (2) injection of non-equilibrium gas (dry or enriched) into a black oil reservoir to mobilize oil by vaporization into a more mobile gas phase or by condensation through an outright (single-contact) or dynamic (multiple-contact) irascibility, and (3) injection of $CO_2$ into an oil reservoir to mobilize oil by miscible displacement and by oil viscosity reduction and oil swelling.

In the recent years, exploration, drilling and production activities have ramped up significantly in unconventional resource plays such as Eagle Ford, Bakken, Permian, Barnett, and others around the world. In the past, fluid homogeneity in a hydrocarbon reservoir has been assumed. There is now a growing awareness that fluids are often heterogeneous or compartmentalized in the reservoir, but still very little detailed understanding of the variation in petroleum fluid quality both vertically and laterally in a play. As relatively unexplored resource plays are being developed, the capability of understanding and predicting petroleum fluid variation and phase behavior would be extremely useful in resource mapping and planning development strategies.

However, the complexities arising from petroleum fluid heterogeneity along the several thousands of feet lateral wellbore in unconventional shale reservoirs adds additional uncertainties to the compositional model. Thus, there exists a need for improved modeling abilities for full reservoir petroleum fluid phase behavior properties and predictions for large shale reservoirs. Ideally, this method can utilize data collected during drilling to dynamically monitor the system.

SUMMARY OF THE DISCLOSURE

This summary is provided to introduce a selection of concepts that are further described below in the detailed description. This summary is not intended to identify key or essential features of the claimed subject matter, nor is it intended to be used as an aid in limiting the scope of the claimed subject matter.

Described herein are methods for predicting petroleum reservoir fluid phase behavior and properties before and during production. Specifically, geochemical data is collected on the front end while drilling unconventional shale resource plays and is used to determine fluid properties. From there, an equation-of-state (EOS) fluid model is developed for modeling the reservoir fluid and the calculated properties can be fine-tuned with the collected data. The model can then be updated as more data is collected through the completion process. This provides a new way for characterizing reservoir petroleum fluids in complicated unconventional shale resource plays with significant reservoir fluid heterogeneity.

The complexities' arising from petroleum fluid heterogeneity along the several 1000's foot lateral wellbore in unconventional shale-gas condensate shale oil wells adds another layer of uncertainty to this problem. These new methods better account for the impact of this variability in reservoir fluid property behavior prediction in unconventional shale resource plays. How these heterogeneities impact fluid phase behavior and results from pressure, volume, temperature (PVT) analyses of recombined produced fluids remains critical since produced fluids used for PVT analyses are commingled.

The methods described herein can be used to predict fluid properties such as saturation pressures and phase prediction, dry and wet gas formation volume factors, oil formation volume factor, and viscosity with minimum geochemical input. The methods apply a probabilistic approach for evaluating variation in the estimated fluid properties, particularly in areas near the oil/gas boundary. Uncertainties exist in the algorithms used in geochemistry based phase predictions. For any given plot of geochemical data, the best-fit line contains some collected data with the rest remaining within the uncertainty boundaries of the best fit line. This uncertainty increases when data is needed to calculate other information or when there are hydrocarbon phase changes in the reservoir. The methods herein attempt to understand the fluid behavior for samples that fall within the uncertainty boundaries, particularly those taken near the oil/gas boundary. By doing so, a much more accurate predictive model can be made with minimum geochemical input.

In more detail, gas isotube samples are taken from select locations along the reservoir or core cuttings/extracts are obtained during drilling and analyzed to determine the thermal maturity (% RO) using known carbon isotope techniques for C1-C8+ hydrocarbons. Thermal maturity refers to the organic maturity and can signify "hot spots" for hydrocarbons.

In the present method, the % RO is used to calculate at least one fluid property. The % RO is input into a workflow, wherein the workflow uses the % RO to estimate fluid properties such as gas-to-oil ratio (GOR), gas-condensate ratio (GCR) and API gravity via a set of predetermined correlations. The correlations in the present method were created using data from an unconventional shale play and can be easily modified for other reservoirs. Alternatively, any suitable correlation can be used.

The workflow uses the estimated CGR/GOR and API for a reservoir fluid from % RO to determine the composition and gas gravity of the hydrocarbons. Published correlations can be used to calculate molecular weights, densities and critical properties of components C1 to C6. Molecular weight and density of C7+ hydrocarbon fraction can be calculated using correlations developed in this work or any other correlation. C7+ fraction is then split into C7 to C80 hydrocarbon components and their mole fractions of can be determined using a logarithmic distribution of mole fractions and performing mass balance on molecular weight. Critical properties of heavier hydrocarbon fractions can be calculated using correlations published in literature or any other correlation. The components are then lumped into pseudo-components for easier modeling.

From there, the C1-C6 components and C7+ pseudo-components are used to build an initial EOS model. The separator gas gravity, gas-to-oil ration (GOR), gas-condensate ratio (GCR) and API gravity values predicted by the EOS model are then compared with the estimated values from % RO to fine tune the EOS model.

Once tuned, a final EOS model is prepared. As the reservoir play is developed, new geochemical data can be compared with the EOS model to dynamically fine-tune the model and thus its predictive accuracy.

There are many advantages of this new workflow method. This methodology provides an avenue for defining fluid phase behavior properties in unconventional reservoir plays, including shale plays, with relatively limited geochemical data. Further, the capability of real time fluid properties estimation while drilling gives significant competitive advantage, especially during land acquisition and acreage positioning during exploration and play appraisal. Finally, the methodology can potentially find significant application in relatively unexplored shale plays where PVT/production data is very limited.

The method can be used with any commercially available software capable of performing compositional flash calculations, including e.g., Eclipse (Schlumberger), GEM or Stars (Computer Modeling Group) and tNavigator (Rock Flow Dynamics), PVTsim (Calsep), or as a standalone tool.

The workflow was exemplified herein as Microsoft Excel-based and all the calculations were performed using a code written in Visual Basic (macros). However, other suitable software package can be used. A flash code/algorithm is needed to perform flash calculations using the EOS developed in the workflow and any general flash code can be added to it.

Any equation-of-state model can be used, but cubic EOS are preferred, including Boyle, Van der Waals, Redlich-Kwong (RK), Soave-Redlich-Kwong (SRK), Peng-Robinson (PR), Peng-Robinson-Stryjek-Vera (PRSV), Peng-Robinson with Peneloux volume shift (PR78), Patel-Teja (PT), Schmit-Wenzel (SW), and Esmaeilzadeh-Roshanfekr (ER). The preferred EOS is Peng-Robinson with Peneloux volume shift (PR78), which is an extension of Peng-Robinson EOS with volume correction.

The geochemical data needed for the initial input can be determined using well-known techniques in the art. Typically, carbon isotope information is obtained for gas samples collected using isotubes and/or mud gas samples or from n-alkane distributions found in cuttings/core extracts. However, the isotope information can also be determined from hydrocarbon gas isotope data obtained from produced fluids. Once the carbon isotope information is known, that the thermal maturity (% RO) can be determined and used to calculate or estimate the remaining fluid properties needed for the EOS model. This limited input data can be beneficial when trying to predict fluid behavior in an unexplored play.

Another advantage of the present methodology is the use of lumped or pooled components. EOS models are used to describe reservoir fluid phase behavior in mathematical format. However, it requires several key parameters for each component in the system, thus making it very impractical to fully model a full reservoir. The present method incorporates lumping or grouping, wherein each pseudo-component is treated by the simulation as a single component. The components are selected for lumping into a pseudo-component based on a common characteristic within a given range (e.g., volatility, molar mass). The present methods can utilize any pooling scheme. Pooled or grouped components are called "pseudo-components" herein.

The correlations used in the presently exemplified workflow to estimate the gas gravity, gas-to-oil ratio (GOR), gas-condensate ratio (GCR) and API gravity from thermal maturity (% RO) values were developed using data from an unconventional shale play. However, any suitable set of correlations can be used in the method.

As used herein, "play" and "reservoir" are used interchangeably to refer to an area in which hydrocarbon accumulations or prospects of a given type occur.

As used herein, "critical properties" refers to the critical temperature, critical pressure, critical volume and acentric factor of a given component. The "critical temperature" is the temperature at and above which vapor of the substance cannot be liquefied, no matter how much pressure is applied. The "critical pressure" of a substance is the pressure required to liquefy a gas at its critical temperature. The acentric factor is a measure of the non-sphericity (centricity) of molecules.

As used herein, "workflow" refers to a series of steps that are performed in order to achieve a task. Typically, those steps must be performed in a particular order, although there are some exceptions.

As used herein, "lumping" refers to "grouping" or "pooling" of one or more components in a system as a means of simplification of a system to reduce the state space of the system to a finite dimension. As an example, C3-C4, C5-C6, and C7+ components can be grouped. As another example, C1-C2, C3-C4, C5-C8, C9-C12, and C13+ is another pooling scheme. Yet another pooling scheme is C1, C2, C3, C4, C5-6, C7-8 and C9+.

As used herein, "tuning" a model refers to refining or training a model by adjusting it to better fit actual data. Exemplary tuning methods include e.g., regression routines in commercial PVT software, such as PVTSim or developed in this work.

The actual data used for model tuning or training can be referred to as a "training set". In statistical modeling, a training set is used to fit a model that can be used to predict a "response value" from one or more "predictors." The fitting can include both variable selection and parameter estimation. Statistical models used for prediction are often called regression models, of which linear regression and logistic regression are two examples.

As used herein, an "equation of state" is a thermodynamic equation describing the state of matter under a given set of physical conditions. It is a constitutive equation that provides a mathematical relationship between two or more state functions associated with the matter, such as its temperature (T), pressure (p), volume (V), or internal energy (e). Equations of state are useful in describing the properties of fluids, mixtures of fluids, solids, and even the interior of stars.

Such equations include Boyles law (pV=constant); Charles law (V1/T1=V2/T2); Daltons law of partial pressures ($p_{total}$=$p_1$+$p_2$+ . . . +$p_n$); the ideal gas law (pV=nRT, R is the gas constant, n=moles).

Cubic equations of state are also possible, including Van der Walls, Redlich Kwong, the Soave modification of Redlich-Kwong, the Peng-Robinson equation of state, Peng-Robinson-Stryjek-Vera equations of state, and the Elliott, Suresh, Donohue equation of state.

Non cubic equations of state include the Dieterici equation of state, the Virial equation of state, and the Benedict-Webb-Rubin equation. Multiparameter equations of state (MEOS), such as the Helmholtz Function form, are also possible, as are other specialized EOS (see e.g., wikipedia.org/wiki/Equation_of_state, incorporated by reference herein in its entirety for all purposes).

'Smart EOS' and 'pseudo-EOS' have been used interchangeably to refer an EOS model for reservoir fluid developed using geochemical data. The "pseudo-EOS" model uses lumped pseudo-components to simplify calculations.

The "final-EOS" model by contrast is the model obtained after tuning or training the pseudo-EOS model. By "final," we do not mean to imply that the model cannot undergo continual refinement as additional samples are collected during production or drilling, but only that the model has been tuned at least once and can be used for various calculations.

"Binary interaction coefficients" or "BICs" refer to coefficients that take into account the non-ideal interaction between components that do not follow the ideal Van der Waals mixing rule, e.g., polar components.

The use of the word "a" or "an" when used in conjunction with the term "comprising" in the claims or the specification means one or more than one, unless the context dictates otherwise.

The term "about" means the stated value plus or minus the margin of error of measurement or plus or minus 10% if no method of measurement is indicated.

The use of the term "or" in the claims is used to mean "and/or" unless explicitly indicated to refer to alternatives only or if the alternatives are mutually exclusive.

The terms "comprise", "have", "include" and "contain" (and their variants) are open-ended linking verbs and allow the addition of other elements when used in a claim.

The phrase "consisting of" is closed, and excludes all additional elements.

The phrase "consisting essentially of" excludes additional material elements, but allows the inclusions of non-material elements that do not substantially change the nature of the invention.

| The following abbreviations are used herein: | |
|---|---|
| ABBREVIATION | TERM |
| EOS | Equation-of-states |
| CGR | Condensate to gas ratio |
| GOR | Gas-oil ratio |
| % RO | Thermal maturity |
| PVT | Pressure, volume, temperature |
| API | American Petroleum Institute - used as a measure of petroleum gravity |
| BIC | binary interaction coefficients |

DESCRIPTION OF EMBODIMENTS OF THE DISCLOSURE

The application provides a novel method for predicting fluid behavior and properties in a reservoir with minimal geochemical data.

The present method includes any of the following embodiments in any combination(s) of one or more thereof:

A method of predicting fluid phase behavior in a reservoir comprising:

a. obtaining at least one sample of a reservoir fluid from a reservoir;
b. estimating the thermal maturity (% RO) of said reservoir fluid;
c. estimating the API gravity, a condensed gas ratio (CGR), and a gas to oil ratio (GOR) of said reservoir fluid using a predetermined correlation with said % RO;
d. estimating a hydrocarbon component composition from C1 to C6 and a C7+ fraction, and gas gravity of said reservoir fluid from said API gravity and said CGR and said GOR;
e. obtaining critical properties for each of the C1-C6 components from literature in said composition of reservoir fluid;
f. splitting said C7+ fraction in to C7 to Cn (where n>7). Estimating the mole fractions and critical properties for C7 to Cn components in said composition of said reservoir fluid;
g. reducing the number of hydrocarbon components by lumping hydrocarbon components based on any lumping method to form one or more lumped components;
h. building a pseudo equation-of-state (EOS) model using with the compositions, critical properties, Peneloux volume shift parameters and binary interaction parameters for the pure and lumped components along with EOS constants for a given EOS model;
i. comparing pseudo-EOS model calculations with the estimated CGR/GOR, API and gas gravity in steps c-d along with any other measured data;
j. tuning the pseudo-EOS model until the model calculations are within predetermined tolerance limits of said calculations in steps c-d to create a final-EOS model; and,
k. predicting fluid phase behavior and properties with said final-EOS model.

A method as herein described, wherein said critical properties are critical temperature, critical pressure, critical volume and acentric factor.

A method as herein described, wherein the equation of state is selected from the group consisting of Boyle, Van der Waals, Redlich-Kwong (RK), Soave-Redlich-Kwong (SRK), Peng-Robinson (PR), Peng-Robinson-Stryjek-Vera (PRSV), Peng-Robinson with Peneloux volume shift (PR78), Patel-Teja (PT), Schmit-Wenzel (SW), and Esmaeilzadeh-Roshanfekr (ER). Preferably, the equation of state is Peng-Robinson with Peneloux volume shift (PR78).

A method as herein described, wherein said tuning step uses Lohrenze-Bray-Clark correlations to tune the viscosity.

A method as herein described, wherein said tuning uses a regression algorithm. Preferably, a linear regression analysis.

A method as herein described, wherein said tolerance limits are 1-10%, <10%, <8%, preferably <5%, <4%, <3%.

A method as herein described, wherein said pseudo components include at least C1, C2, C3, C4, C5, C6, and C7+ or include at least C1, C2, C3, C4, C5-6, and C7-8 and C9+ or include at least C1, C2, C3-4, C5-6, C7-8, C8-12, C13-16 and C17+. In preferred embodiments, all C4 components are grouped, as are C5 on up to C6 and then C7+ components are grouped into larger components containing two or more carbon groups in each lumping.

A method as herein described, wherein a plurality of % RO values from a plurality of reservoir fluid samples are inputted.

A method as herein described, wherein said final EOS model is further tuned with additional measurements obtained from said reservoir.

A non-transitory machine-readable storage medium, which when executed by at least one processor of a computer, performs the steps of any method herein described.

It is not uncommon for some properties of a reservoir fluid to change over the operation of a well. Such changes can include the percentage of liquid to gas and other properties of the fluid. The EOS for a specific sample of a reservoir fluid can be used to determine what changes are likely to occur to the reservoir fluid over the life of the well. This predictive information can be quite valuable to the reservoir engineer in charge of field operations, who can then make decisions necessary for optimizing the field's production based on the information.

Certain EOS formulas can be more predictive compared to other EOS formulas. For example, research has shown that non-cubic equation of states can describe the volumetric behavior of pure substances well, but may not be the best equations for complex hydrocarbon mixtures, such as reservoir fluids. Moreover, a single EOS may not be able to predict all the thermodynamic properties of different kinds of reservoir fluids. As such, the EOS may need to be selected based on the exact composition of the fluid.

The present application describes a new workflow for creating an EOS model that is tuned using real data from the reservoir. The model can be repeatedly tuned as the reservoir is developed for more accurate modeling.

Figure 1:
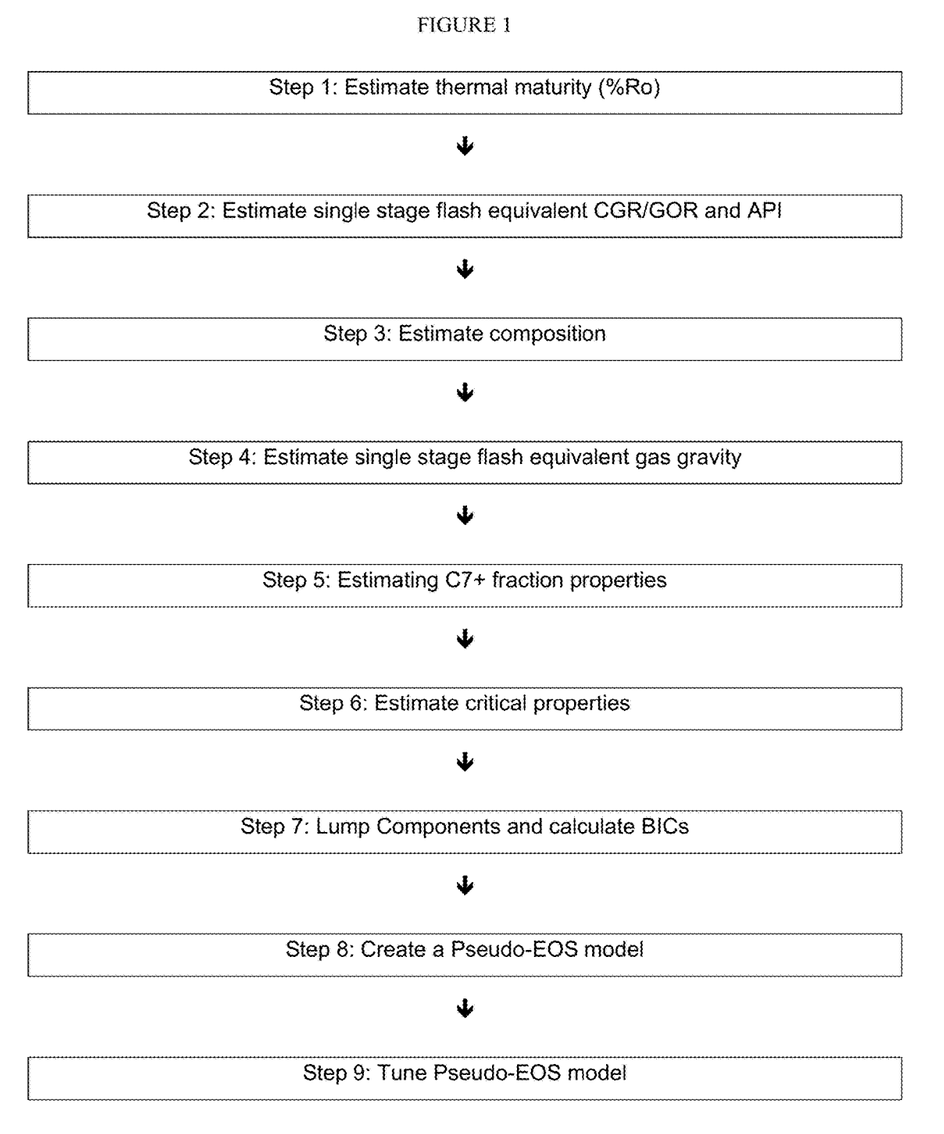
FIG. 1. Steps in the workflow according to one embodiment of the present disclosure.

A schematic of the 9 steps in the presently described workflow is shown in FIG. 1 and described below:

Step 1: Estimate or Determine Thermal Maturity (% Ro):

Thermal maturity is the degrees of heating of a source rock in the process of transforming kerogen into hydrocarbon. This value can be determined from the C-isotope data of the hydrocarbons collected from mud gas while drilling using isotubes or oil/cutting extracts obtained while drilling. For collected isotube samples, thermal maturity is determined using the C-isotope values of a pair of hydrocarbon molecules such as C1-C2 (Methane and Ethane) or C2-C3 (Ethane and Propane) using well-established geochemistry approach in the literature. Other equations exist to estimate % RO from cuttings/core extracts with n-alkane distribution. As these approaches are well-known in the industry, they will not be described here.

Figure 2A:
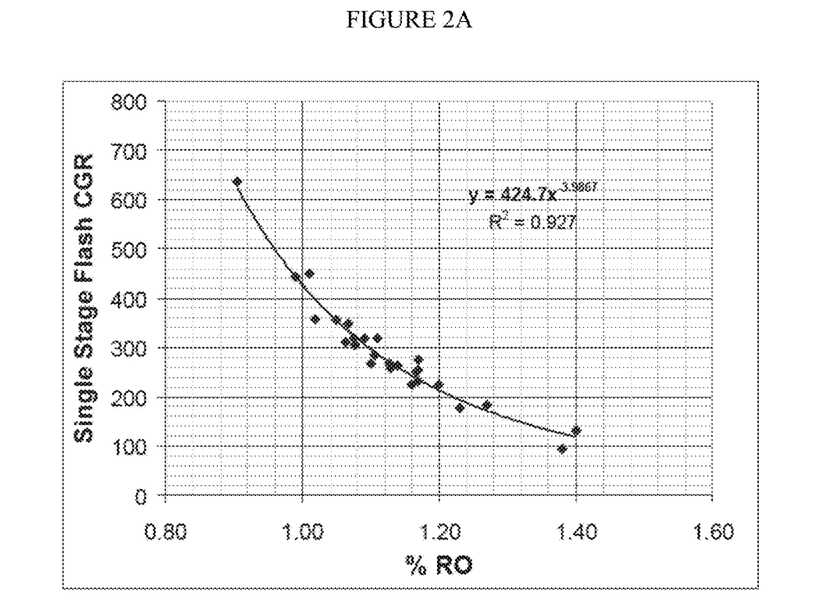
FIG. 2A. Correlation of Single Stage Flash CGR and % RO for a shale reservoir.
Figure 2B:
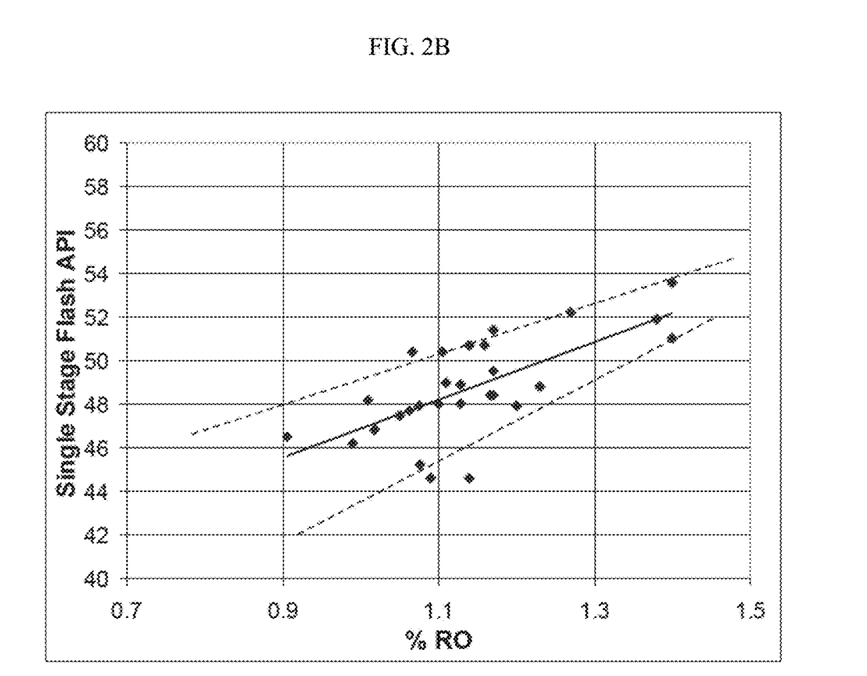
FIG. 2B. Correlation of Single Stage Flash API and % RO for a shale reservoir.

Step 2: Estimate Single Stage Flash Equivalent CGR, GOR and API:

The estimation is based on the thermal maturity ratio. Correlations have been developed based on the shale play example described below and FIGS. 2A-B display these correlations for CGR/GOR (FIG. 2A) and API (FIG. 2B). As can been seen, there is a strong positive correlation between API and % RO, but an exponential decay is seen between CGR and % RO. These correlations can easily be calibrated for any other shale resource play.

Step 3: Estimate Composition:

The composition of the reservoir fluid is calculated in step 3 using the estimated CGR and API gravity. Correlations have been developed in this work to calculate the mole fraction of various components (C1 to C6 and C7+ fraction) in the reservoir fluid using API gravity and CGR/GOR.

Step 4: Estimate Single Stage Flash Equivalent Gas Gravity:

Correlations have been developed to estimate the single stage flash equivalent gas gravity using the estimated CGR/GOR, API and the compositions from steps 3. This estimated gas gravity along with estimated CGR/GOR and API from % RO are used as the training set for regression step 9.

Step 5: Estimating C7+ Fraction Properties:

C7+ mole fractions are calculated using estimated gas gravity and CGR/GOR using the correlations developed in this work. C7+ molecular weight and density is calculated using the estimated API gravity using correlations developed in this work. C7+ fraction is then split into C7 to C80 hydrocarbon components. Here C7 refers to a combination of hydrocarbon components with 7 carbons such as heptane and other isomers and C80 refers to components with 80 carbons. Molecular weight and densities of C7 to C80 hydrocarbon components are taken from literature or can be calculated using published literature. The mole fraction of C7 to C80 hydrocarbon components is calculated assuming a logarithmic distribution of C7+ mole fractions and performing mass balance on C7+ fractions and honoring the estimated C7+ molecular weight. Densities of C7 to C80 fractions are calculated assuming logarithmic distribution of C7+ fractions and honoring the average C7+ density calculated from developed correlation using API. The method is also applicable for any other type of C7 plus fraction distribution, such as Gamma distribution etc. and up to any carbon fraction.

Step 6: Estimate Critical Properties:

The molecular weight, critical properties and volume shift parameters (Peneloux volume correction factors) of components from methane to hexanes are well known and taken from literature. Molecular weight of C7 to C80 components is estimated in step 6. Critical properties and Peneloux volume shift correction for C7 to C80 hydrocarbon components can then be calculated using correlations published in literature or any other correlation.

Step 7: Lump Components and Calculate BICs:

Compositional simulation can be extremely time-consuming and costly due to the large number of components. Therefore, pseudo components are commonly used instead. Components from C1 to C80 can be lumped. For example, C1, C2, C3-C4, C5-C6, C7-C10, C11-C15, C16-C24, C25-C80 etc. can be lumped to reduce number of components in an EOS model. These lumped components are called as pseudo components. Lumping pure components to form pseudo components is a common practice in developing EOS models. Properties of the pseudo components are calculated by taking the mole fraction weighted average of the hydrocarbon component's properties. The method can also be used with different lumping schemes for a variety of carbon numbers.

The binary interaction coefficients (BICs) between components are assumed as zero between hydrocarbon components. However, other suitable correlations for binary interaction coefficients or data or values can be used in the model.

Step 8: Create a Pseudo-EOS Model:

Steps 1 through 6 estimates mole fractions, molecular weights, densities, binary interaction coefficients, critical properties including critical pressures, critical temperatures, acentric factors, critical volumes and Peneloux volume shift parameters for the pure and lumped pseudo components.

These estimated properties along with the equation of constants, which are well defined in literature for different types of EOS models, is an EOS for a given fluid. As the EOS is not yet tuned against any measured PVT data, it is referred as a "pseudo-EOS" for a given fluid.

EOS is a compilation of all the properties described in above steps. It basically is a set of components and their properties that are fed in to one of the cubic EOS models (listed in ¶0081 below). In the oil & gas industry, this set of components and their properties is generally referred as an EOS for a given fluid.

Any EOS can be used including Boyle, Van der Waals, Redlich-Kwong (RK), Soave-Redlich-Kwong (SRK), Peng-Robinson (PR), Peng-Robinson-Stryjek-Vera (PRSV), Patel-Teja (PT), Schmit-Wenzel (SW), and Esmaeilzadeh-Roshanfekr (ER). In this work Peng-Robinson EOS with Peneloux volume correction was used.

There are several software packages already on the market that can be modified to be used with the method, e.g., PVT Pro equation-of-state software by Schlumberger, the PVTP tool by Petroleum Experts, PVTSim from CalSep, PhazeComp by Zick tech., and the like. The High Pressure Processes Group also presents set of open source MATLAB programs for the calculation of phase equilibrium and other thermodynamic properties using different equations of state (classical cubic equations, cubic equations with excess Gibbs energy mixing rules, group contribution equations and SAFT equations).

The hardware requirements for such programs tend to be modest. To run PVTsim, for example, minimum hardware requirements include: 1 Gb RAM and 1 Gb free disk space, 1280×800 pixels screen resolution, and a Windows operating system including Windows Vista, Windows 7, and Windows 8. Of course, faster processing can be achieved with better systems.

Step 9: Tuning Pseudo-EOS Model:

The predictive information obtained from the pseudo-EOS can then be improved by fine tuning the EOS. If a set of physical data is available, it can be used to tune the pseudo-EOS model. In this work, the estimated CGR/GOR, gas gravity and API from steps 2 and 4 were used as a reference data to tune the EOS model. If single stage separator or multi-stage separator flash data for fluid sample is available, then that can be used as the reference data to tune the EOS model instead of, or in addition to, the data from step 2, 4.

Using the pseudo-EOS model developed through step 8, reservoir fluid is flashed (flash calculation is standard terminology in PVT) at 14.7 psi and 60° F. using a cubic EOS solver, such as Michelsen's method or any other. The calculated CGR/GOR, gas gravity and API are then compared to the values from steps 2 and 4. Other data measured from reservoir samples can also be used in the tuning method. Flashing the fluid from reservoir conditions directly to standard conditions, 14.7 psi and 60° F. is generally referred as "single stage flash." The fluid compositions, binary interaction parameters, Peneloux volume shift parameters and the critical properties of pure and pseudo components are then regressed until the difference between the calculated and reference CGR/GOR, API and gas gravity are within pre-determined tolerance limits. Critical properties of lighter hydrocarbons (C1 to C6) need not be not tuned as they well known. This tuning process improves the predictability of the EOS.

A regression algorithm was developed in this work to tune the EOS, however any other regression algorithm (available in most of the commercial PVT software such as PVTSim, etc.) can also be used for tuning.

In addition, tuning the critical volume of components based on oil viscosity can also occur. The tuning method we tested used Lohrenz-Bray-Clark (LBC) correlations, but tuning can be done with any other viscosity correlation for calculating fluid viscosity. The critical volumes of components are tuned to match the stock tank oil viscosity. If the stock tank oil viscosity is not known, it is calculated using correlations published in literature or developed in this work or any other suitable viscosity correlation.

Regression can also be performed to match any other measured fluid data, such as saturation pressure, multi-stage separator test data, differential liberation test, constant composition expansion, constant volume depletion, slim tube test, minimum miscibility pressure, etc.

For tuning, the calculated information is compared to the estimates from the EOS model. The EOS model is slowly changed to bring the estimates within a predetermined tolerance limit of the calculated information. The tolerance limits are judgment based, and usually are specified by the user. In this study, a tolerance of +/−1.5% on gas gravity, +/−2% on GOR/CGR and +/−5% on API was used.

Step 9: Final Smart-EOS Model:

The regressed EOS is referred as the final Smart/pseudo EOS model here. This model can then be used for predicting fluid phase behavior and properties. If desired, the model can be further tuned when additional data becomes available, or it can continue to be used as is.

The present method is exemplified with respect to an unconventional shale play. However, this is exemplary only, and the present method can be broadly applied to any reservoir. The following discussion is intended to be illustrative only, and not unduly limit the scope of the appended claims.

UNCONVENTIONAL SHALE PLAYS

In unconventional shale plays petroleum fluid types and composition changes substantially both laterally and vertically within the formation. Geochemical analysis of gases collected while drilling and oil extracts from cores/cuttings indicate that significant fluid quality changes can also be observed along the long horizontal well drilled within the formation. Fluid samples collected at a given time from these wells during production often represent the average properties of the fluid flowing from different regions of the well bore and therefore, most of the time are insufficient to quantify the variation in fluid properties.

Understanding fluid heterogeneity along the well bore and its implications for accurate prediction of the variation of fluid behavioral properties, such as the phase, saturation pressure, formation volume factors, viscosity, and others, are commonly needed in resource mapping, oil/gas in-place estimations, reservoir simulations for predicting reservoir performance. The presently described method was tested and validated using fluids data from an unconventional shale play.

Several gas samples were collected along the well bore while drilling (before comingling) allowing us to use the derived gas geochemistry to predict the phase behavior of the in-situ fluid and stochastically predict overall fluid behavior of any well in question. These initial samples were used to build correlations between the calculated % RO for each sample and the single stage flash CGR and API.

The best-fit line for both correlations was used in the present workflow to estimate single stage flash CGR, GOR and API for newly acquired samples. Further correlations were developed to calculate hydrocarbon composition from the single stage Flash CGR, GOR and API.

As the play was developed, new mud gas samples were obtained using isotubes and the thermal maturity was determined using the C-isotope values for the C1-C2 hydrocarbon pair. The calculated thermal maturity was used in the equations for the best-fit lines to determine the single stage flash CGR, GOR and API.

Using the estimated single stage flash CGR, GOR and API, the gas gravity and composition of the reservoir fluid was calculated and separated into C1-C6 and C7+ fractions. Steps 3 through 9 as described above were followed to develop a final EOS model.

Figure 3:
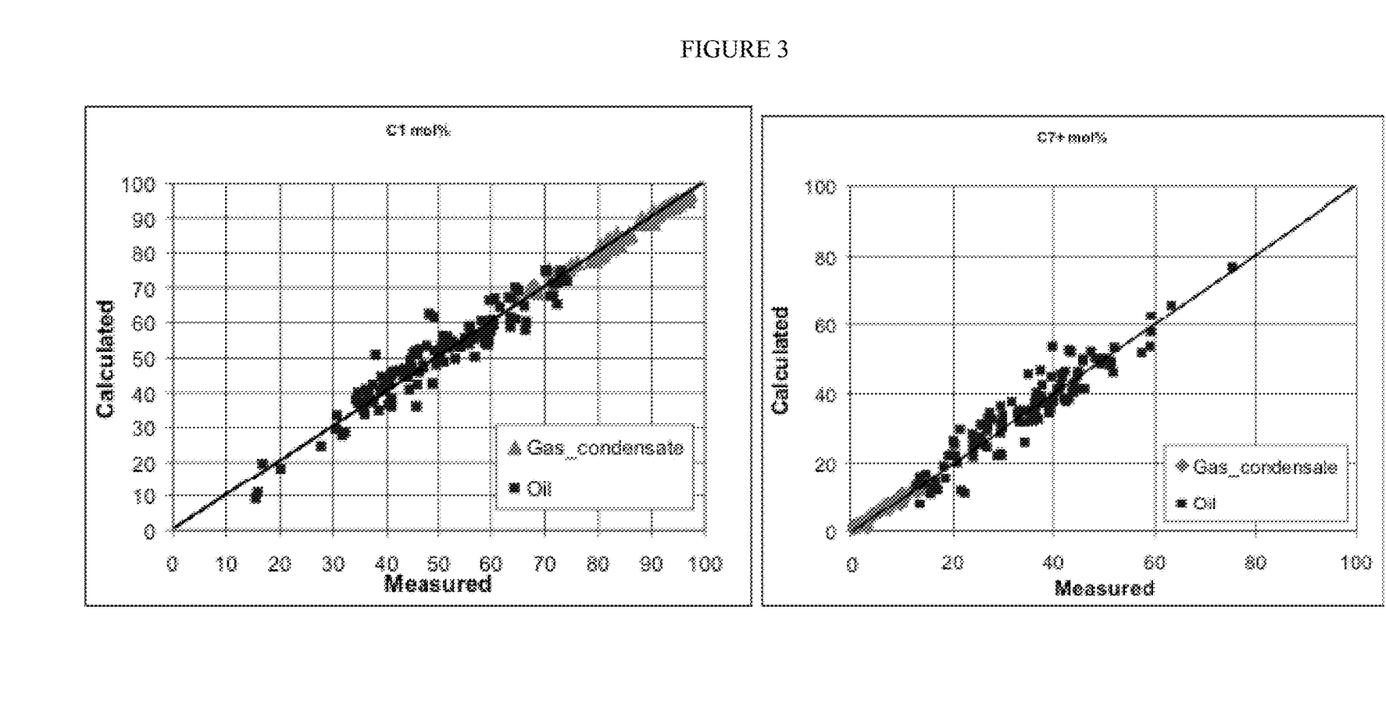
FIG. 3. Comparison of calculated and measured C1 and C7+ mole percentages.

FIG. 3 compares the calculated mole percentages using the above methods with the actual measured percentages for C1, on the left, and C7+, on the right for both oil and gas condensate fluid samples. As can be seen, the calculated mole fractions using thermal maturity data are in good agreement with the measured data.

The resulting final EOS model has become important in subsurface fluid behavior properties prediction (dew point vs. bubble point) and well classification (gas-condensate vs. oil wells), which can have consequences on acreage holding associated with each well. In addition, this new workflow method and EOS modeling affords an understanding of the impact/importance of fluid variability in development strategies, well placement and performance predictions.

Figure 4:
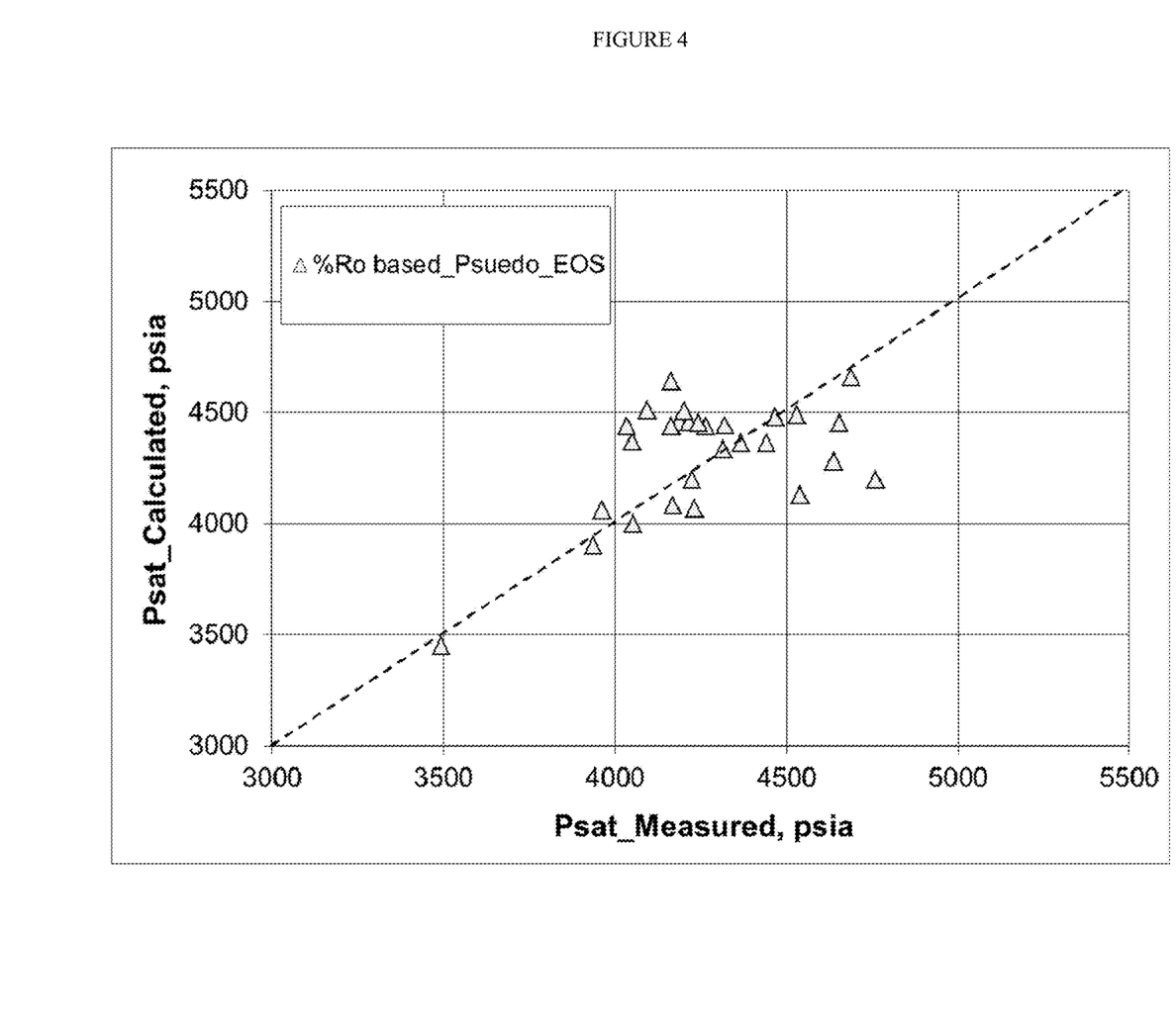
FIG. 4. Comparison of pseudo-EOS model and tuned-EOS model for bubble point (left) and dew point pressures (right).

FIG. 4 compares the measured saturation pressures with the calculations using the pseudo-EOS model. Results show that the calculated saturation pressures for both oil and gas condensate fluids using the pseudo-EOS model, developed just using the thermal maturity ratio (% RO), are in pretty good agreement with the measured data (within +/−500 psi). The results are not expected to match perfectly with the measured data as the whole EOS model was basically built just using % RO.

The EOS model can be built for different well sites to help with fluid properties predictions and updated with real time geochemical data.

SECOND CASE STUDY

Figure 5:
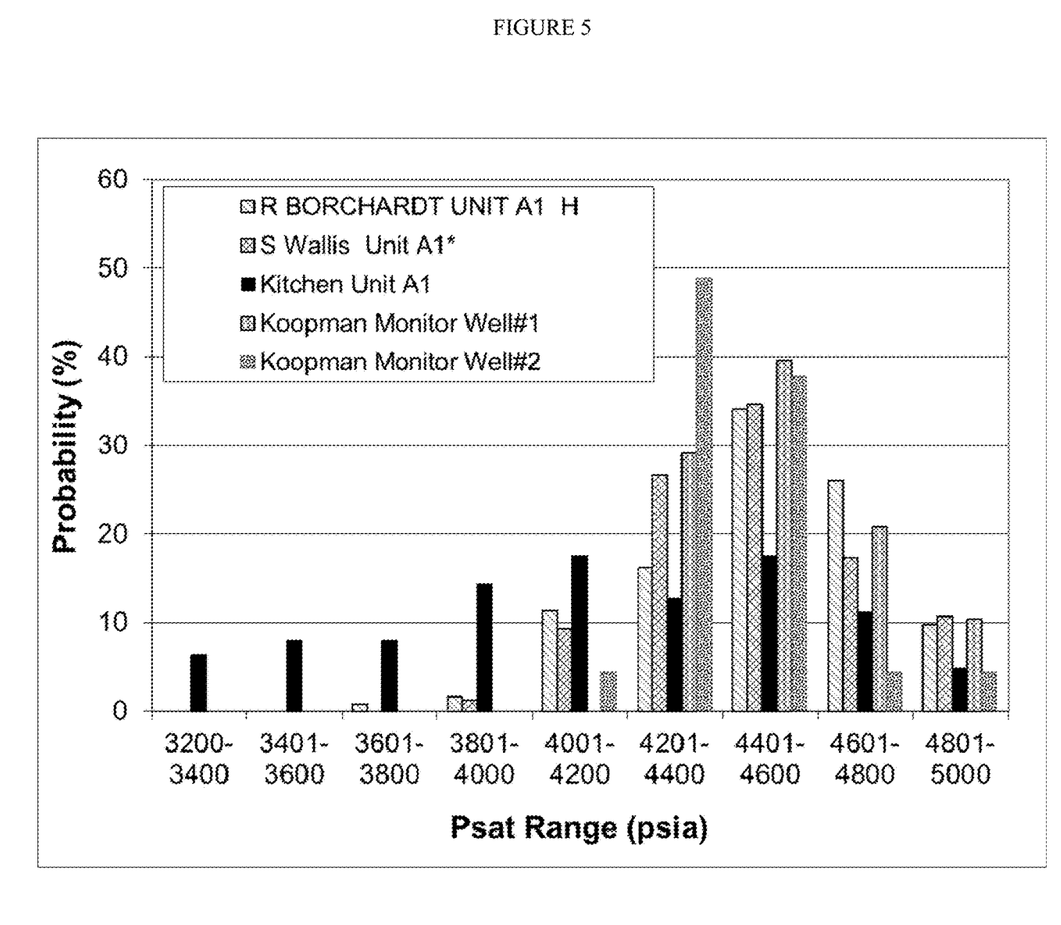
FIG. 5. Probability Distribution of Estimated Saturation Pressure using % Ro variation along the wellbore.

A second case study was performed to further demonstrate the value of the smart-EOS model. FIG. 5 shows the probability distribution of estimated saturation pressure (Psat) the using % RO variation along the wellbore, which was obtained from isotube data of mud gas samples. This graph shows 2 different wells in an unconventional shale play.

Figure 6:
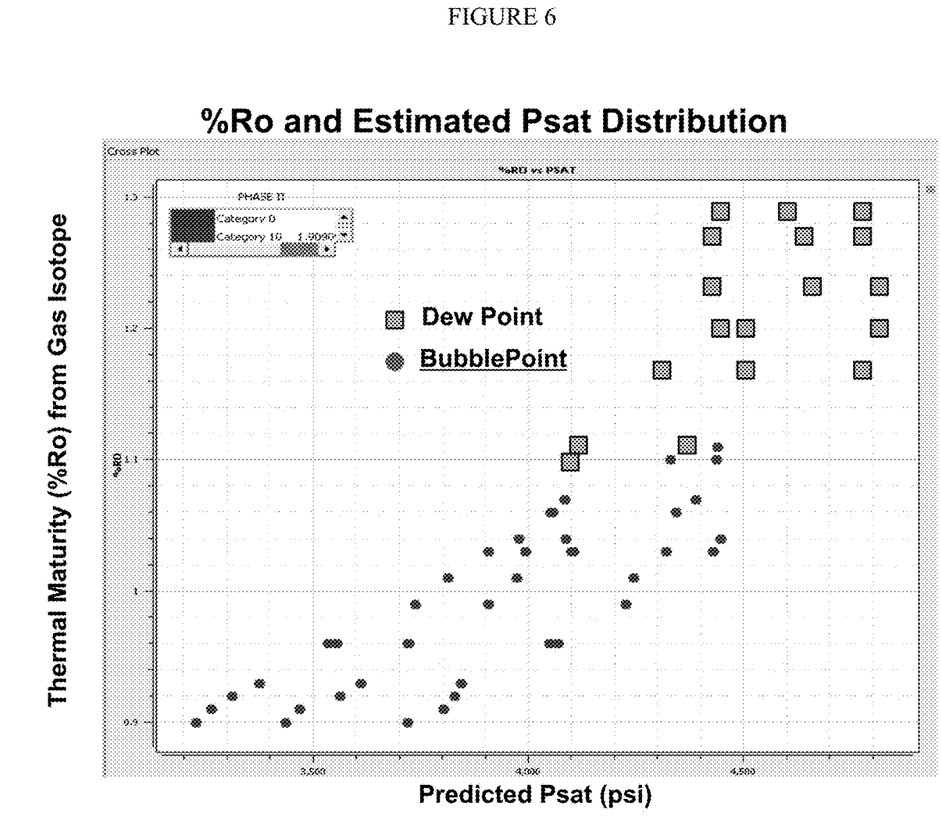
FIG. 6. % Ro and Estimated Psat Distribution for the Kitchen Unit A1.
Figure 7:
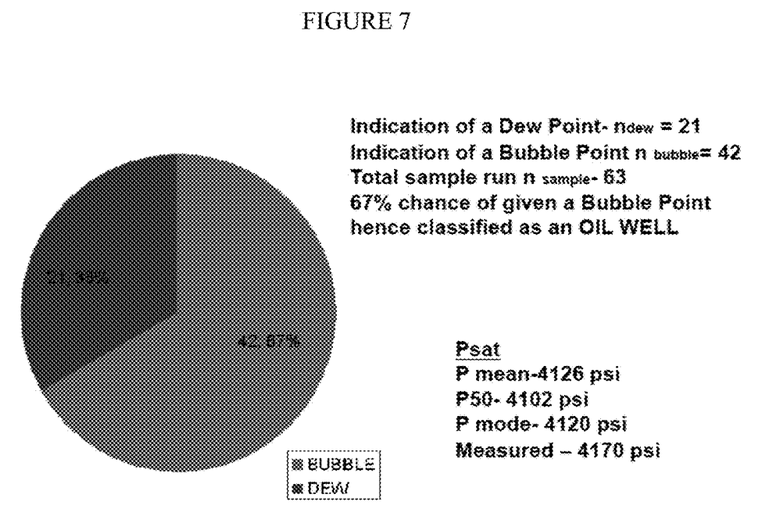
FIG. 7. Probabilistic Phase Prediction for Kitchen Unit 1A.
Figure 8:
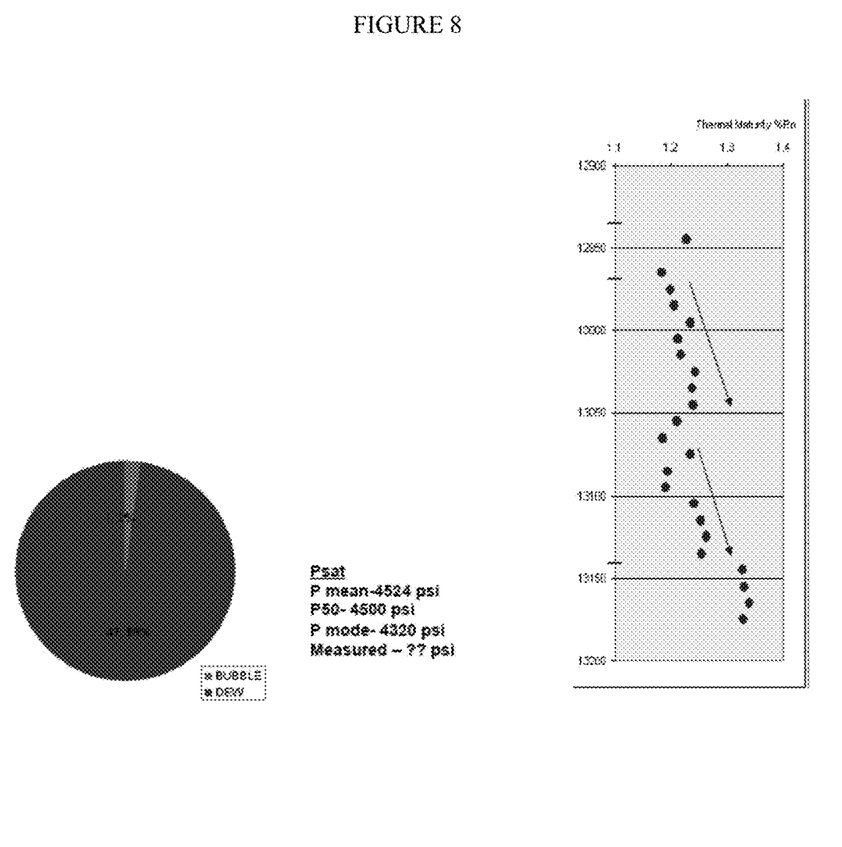
FIG. 8. Probabilistic Phase Prediction for Koopman MW1 (left) and % Ro and Estimated Psat Distribution for same unit (right).

FIG. 6 shows the distribution of bubble (67%) versus dew (33%) and indicates that this is a oil well. The same method was applied in FIG. 7, which shows another well, which is almost all dew, and thus is predicted to be a gas well. Subsequent development confirmed these predictions. These results demonstrate the value of the methodology, as well as the accuracy of the smart-EOS model.

The following references are incorporated by reference in their entirety for all purposes.

US20090071239 Methods for optimizing petroleum reservoir analysis

WO2014025342 Methods of predicting a reservoir fluid behavior using an equation of state U.S. Pat. No. 8,666,667 Hydrocarbon production allocation methods and systems US20120150519 Enhanced oil recovery screening model.

https://en.wikipedia.org/wiki/Equation_of_state.

The invention claimed is:

1. A method of predicting fluid phase behavior in a reservoir, the method comprising:
  extracting at least one petroleum sample from one or more predetermined locations of the reservoir, the at least one petroleum sample including at least one of a reservoir fluid, a mud gas, or core and cutting extracts;

estimating a thermal maturity of the at least one petroleum sample;

estimating an API gravity, a condensed gas ratio (CGR), and a gas to oil ratio (GOR) of the at least one petroleum sample using a predetermined correlation with the thermal maturity;

estimating a hydrocarbon component composition and a gas gravity of the at least one petroleum sample reservoir fluid from the API gravity and the CGR and the GOR, the hydrocarbon component composition comprising C1 to C6 components and a C7+ fraction;

obtaining one or more critical properties for each of the C1 to C6 components in the hydrocarbon component composition of the at least one petroleum sample;

splitting the C7+ fraction in the hydrocarbon component composition of the at least one petroleum sample into C7 to Cn components (where n>7);

estimating one or more mole fractions and one or more critical properties for the C7 to Cn components in the hydrocarbon component composition of the reservoir fluid;

reducing the hydrocarbon component composition of the at least one petroleum sample by lumping one or more hydrocarbon components to form one or more lumped components;

building a pseudo equation-of-state (EOS) model using the hydrocarbon component composition of the at least one petroleum sample, the one or more critical properties of the C1 to C6 components and the one or more critical properties for the C7 to Cn components, Peneloux volume shift parameters and binary interaction parameters for the one or more lumped components and any unlumped components along with EOS constants for a given EOS model;

comparing pseudo EOS model calculations with the CGR, GOR, API and gas gravity;

generating a final EOS model by tuning the pseudo EOS model until the pseudo EOS model calculations are within predetermined tolerance limits of the CGR, GOR, API and gas gravity;

generating a prediction of fluid phase behavior and properties of the reservoir with the final EOS mode; and performing at least one drilling operation at the reservoir based on the prediction of fluid phase behavior and properties.

2. The method of claim 1, wherein the one or more critical properties of the C1 to C6 components or the one or more critical properties for the C7 to Cn components include one or more of critical temperature, critical pressure, critical volume and acentric factor.

3. The method of claim 1, wherein an EOS of the final EOS model is a cubic EOS.

4. The method of claim 1, wherein an EOS of the final EOS model is selected from the group consisting of Boyle, Van der Waals, Redlich-Kwong (RK), Soave-Redlich-Kwong (SRK), Peng-Robinson (PR), Peng-Robinson-Stryjek-Vera (PRSV), Peng-Robinson with Peneloux volume shift (PR78), Patel-Teja (PT), Schmit-Wenzel (SW), and Esmaeilzadeh-Roshanfekr (ER).

5. The method of claim 1, wherein an EOS of the final EOS model is Peng-Robinson with Peneloux volume shift (PR78).

6. The method of claim 1, wherein tuning the pseudo EOS model uses Lohrenze-Bray-Clark correlations to tune viscosity.

7. The method of claim 1, wherein tuning the pseudo EOS model uses a regression algorithm.

8. The method of claim 1, wherein tuning the pseudo EOS model uses linear regression analysis.

9. The method of claim 1, wherein the predetermined tolerance limits are 1%-10%.

10. The method of claim 1, wherein the one or more lumped components include at least C1, C2, C3-4, C5-6, C7-8, C8-12, C13-16 and >C16+.

11. The method of claim 1, wherein the one or more lumped components include at least C1, C2, C3, C4, C5-6, and C7-8 and C9+.

12. The method of claim 1, wherein the final EOS model is further tuned with additional measurements obtained from the reservoir or from one or more additional fluid samples obtained from the reservoir.

13. The method of claim 1, wherein a plurality of thermal maturity values from a plurality of reservoir fluid samples are estimated.

14. The method of claim 1, further comprising:
determining fluid phase behavior and properties with a future EOS model.

15. The method of claim 14, further comprising:
optimizing production of the reservoir based on the future EOS model.

16. A method of predicting fluid phase behavior in a petroleum reservoir, the method comprising:
determining a thermal maturity of at least one petroleum sample extracted from one or more predetermined locations of the petroleum reservoir;

determining a hydrocarbon component composition and a gas gravity of the at least one petroleum sample based on an API gravity, a condensed gas ration (CGR), and a gas to oil ration (GOR) of the at least one petroleum sample, the hydrocarbon component composition comprising C1 to C6 components and a C7+ fraction, the API gravity and the CGR and the GOR each being determined based on the thermal maturity;

splitting the C7+ fraction into C7 to Cn components (where n>7);

reducing the hydrocarbon component composition of the at least one petroleum sample by lumping one or more hydrocarbon components to form one or more lumped components;

building a pseudo equation-of-state (EOS) model using the hydrocarbon component composition of the at least one petroleum sample, one or more critical properties of the C1 to C6 components and one or more critical properties for the C7 to Cn components, Peneloux volume shift parameters and binary interaction parameters for the one or more lumped components and any unlumped components along with EOS constants for a given EOS model;

generating a final EOS model by tuning the pseudo EOS model until pseudo EOS model calculations are within predetermined tolerance limits of the CGR, GOR, API and gas gravity; and performing at least one drilling operation at the petroleum reservoir based on the final EOS model.

17. The method of claim 16, wherein the predetermined tolerance limits are 1%-10%.

18. The method of claim 16, wherein an EOS of the final EOS model is selected from the group consisting of Boyle, Van der Waals, Redlich-Kwong (RK), Soave-Redlich-Kwong (SRK), Peng-Robinson (PR), Peng-Robinson-Stryjek-Vera (PRSV), Peng-Robinson with Peneloux volume shift (PR78), Patel-Teja (PT), Schmit-Wenzel (SW), and Esmaeilzadeh-Roshanfekr (ER).

19. The method of claim 16, wherein an EOS of the final EOS model is Peng-Robinson with Peneloux volume shift (PR78).

20. The method of claim 16, wherein the pseudo EOS model includes viscosity predictions and tuning the pseudo EOS model uses Lohrenze-Bray-Clark correlations to tune viscosity.

21. The method of claim 16, wherein tuning the pseudo EOS model uses a regression algorithm.

22. The method of claim 16, wherein the final EOS model is further tuned with additional measurements obtained from the reservoir.

* * * * *